United States Patent
Roth

(10) Patent No.: US 7,846,470 B2
(45) Date of Patent: Dec. 7, 2010

(54) FEED OR FEED ADDITIVE CONTAINING AN ALKALOID

(76) Inventor: Hermann Roth, Kiedricher Strasse 35 c, D-65343 Eltville (DE)

( * ) Notice: Subject to any disclaimer, the term of this patent is extended or adjusted under 35 U.S.C. 154(b) by 263 days.

(21) Appl. No.: 11/596,788

(22) PCT Filed: May 6, 2005

(86) PCT No.: PCT/EP2005/004946

§ 371 (c)(1), (2), (4) Date: Dec. 27, 2007

(87) PCT Pub. No.: WO2005/115165

PCT Pub. Date: Dec. 8, 2005

(65) Prior Publication Data

US 2008/0234312 A1    Sep. 25, 2008

(30) Foreign Application Priority Data

May 19, 2004   (AT) ................................ A 882/2004

(51) Int. Cl.
*A23K 1/16* (2006.01)
(52) U.S. Cl. ..................................................... 424/442
(58) Field of Classification Search .................... None
See application file for complete search history.

(56) References Cited

U.S. PATENT DOCUMENTS 4,769,452 A * 9/1988 Boulware ................... 540/476
2003/0190344 A1 * 10/2003 Roth .......................... 424/442

OTHER PUBLICATIONS

Sanguinaria Canadensis L., Jun. 25, 2002 (by wayback machine), pp. 1-2.*
Greenfield, Jackie and Jeanine M. Davis, Collection to Commerce: Western North Carolina Non-Timber Forest Products and Their Markets,Department of Horticultural Science, last updated: May 9, 2003, pp. 1-112.*
Janbez, K. H., S.A. Saeed and A.H. Gilani, An Assessment of the potential of Protopine to Inhibit Microsomal Drug Metabolising Enzymes and Prevent Chemical Induced Heptatotoxicity in Rodents, Pharmacological Research, vol. 38, No. 3, 1998, pp. 1-5.*
Liu, Hailing, Brett E Jones, Cynthia Bradham and Mark J Czaja, Increased cytochrome P450 2E1 expression sensitizes hepatocytes to c-Jun-mdiated cell death from TNF, Am J Physiol Gastrointest Liver Physiol (Oct. 24, 2001), pp. 1.*
Pedersen, Anni Oyan, Danish Pig Production Report, Feb. 16, 1998, pp. 1-14.*
Zdarilova, Adela, et al., Food and Chemical Toxicology 46 (2008) 3721-3726.*

* cited by examiner

*Primary Examiner*—Robert A Wax
*Assistant Examiner*—Lyndsey Beckhardt
(74) *Attorney, Agent, or Firm*—Jonathan Myers; Andrew Wilford

(57) ABSTRACT

The invention relates to a feed containing conventional feed substances, or feed additives for producing said feed. According to the invention, the feed or feed additive contains a protopine alkaloid, in particular α-allocryptopine, preferably in combination with at least one benzophenanthridine alkaloid in an active quantity as a stimulant and appetite enhancer for commercial animals.

10 Claims, 1 Drawing Sheet

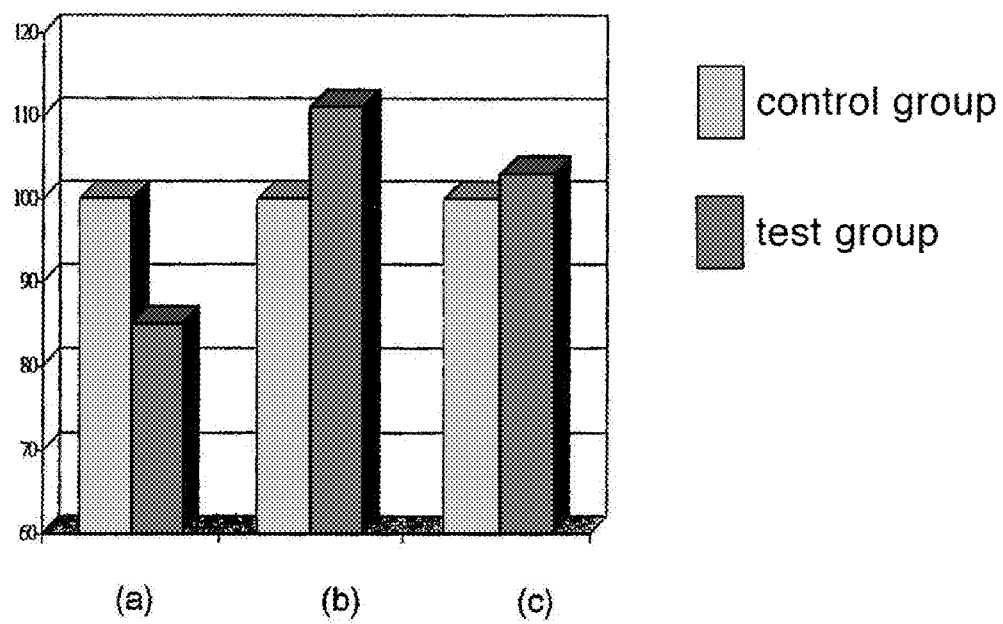
(a) thickness of backfat at last lumbar vertebra
(b) thickness of muscle meat
(c) lean meat ratio

FEED OR FEED ADDITIVE CONTAINING AN ALKALOID

CROSS REFERENCE TO RELATED APPLICATIONS

This application is the US national phase of PCT application PCT/EP2005/004946, filed 6 May 2005, published 8 Dec. 2005 as WO 2005/115165, and claiming the priority of Austrian patent application A882/2004 itself filed 19 May 2004.

FIELD OF THE INVENTION

This invention relates to a feed for appetite stimulation and performance enhancement in livestock, containing conventional feedstuffs, such as cereal or cereal products, maize, proteins and aromatic amino acids, vitamins, mineral additives, such as salts, phosphates, lime, enzymes and the like, as well as to a feed additive for the preparation of such feed.

BACKGROUND OF THE INVENTION

So called performance enhancers are often used when feeding of animals is concerned. These substances optimize the nutrient uptake in rumen and intestine. This way, feed conversion is improved and the consummation per kilogram weight gain is reduced. As far as performance enhancers are concerned, a distinction is drawn between antibiotic, probiotic and chemical performance enhancers.

Lately, the use of performance enhancers, particularly of antibiotic and chemical performance enhancers, has become less accepted by the consumers, but also by some of those skilled in the art, since on the one hand people worry about negative effects on human health caused by residues of the substances used in food of animal origin, and on the other hand people are afraid of developing resistance to microorganisms, particularly to human pathogenic organisms. Also, in some countries many of the substances used as performance enhancers are no longer allowed to be used as feed additives.

On the other hand, it has to be noted that many livestock owners are in favor of the use of performance enhancers, since these substances not only enhance animal growth but can also improve the state of health of the animals. Thus, main attention is now turned to the research on suitable substitutes, such that conventional performance enhancers can be replaced by alternative ones.

The use of benzophenanthridine alkaloids for performance enhancement is known from DE 43 03 099. These alkaloids are particularly contained in *Sanguinaria canadensis*, which, however, is a natural plant material and thus is only available in limited amounts. Thus, these alkaloids are comparatively expensive.

From WO 02/21933 the use of a protoberberine alkaloid in combination with a benzophenanthridine alkaloid as performance enhancer or appetite stimulant for livestock is known.

SUMMARY OF THE INVENTION

Surprisingly it was found that appetite stimulation and performance enhancement can be significantly improved by the use of protopine alkaloids, especially of α-allocryptopine.

The use of α-allocryptopine in animal husbandry had not been known until now.

According to one feature of the invention, a feed of the aforementioned kind or a feed additive or respectively feed additive(s) are provided for the preparation of such feed, containing a protopine alkaloid, especially α-allocryptopine in an effective amount to be used as performance enhancer and appetite stimulant for livestock.

According to a further feature of the invention, the feed or the feed additive can contain a protopine alkaloid, especially α-allocryptopine, in combination with at least one benzophenanthridine alkaloid. Thanks to the use of such alkaloid combinations, it is possible to achieve an unexpected synergy effect.

It is assumed that α-allocryptopine is a hepatoprotective substance. Corresponding literature concerning the use thereof can be found in human medicine. A combination with the benzophenanthridine alkaloids should be considered due to the fact that the effective systems should be synergistic. Benzophenanthridine alkaloids have a minor antimicrobial effect and a protective effect as far as essential nutriments such as tryptophan, lysine, etc. are concerned. α-allocryptopine protects the liver and is probably of regenerative use, a fact which is particularly advantageous in growing animals, in lactation and in poultry, since clinical liver disorders are often diagnosed in these animals (pigs, sows, dairy cows, fatlings) or problems regarding health are typically observed due to the fatty liver syndrome (broilers, layers).

According to one aspect of the present invention, both effects can be combined since a better supply with essential amino acids offers the detoxification leads to the liver being supplied with the necessary substrate. Besides, both this process and the liver metabolism are strongly stimulated due to the combination with α-allocryptopine. Eventually, the processes described herein can result in a synergistic symbiosis characterized by increased performance, better state of health, increased longevity, reduced use of medicinal products and secured environmental, ecological and operational balance.

According to this feature, the invention can exceed the individual effects of the respectively used individual substances benzophenanthridine alkaloid or α-allocryptopine and represent thus progress both for production and consumer.

According to a further feature of the invention, the protopine alkaloid and/or the benzophenanthridine alkaloids can be used in form of plant material, plant juice or in form of extracts of plant material. For example, the α-allocryptopine may be used in form of plant material from *Macleaya cordata* or as extract thereof. Extracts which can be used in this invention may be produced according to any known procedure, and extracts which can be used may be for example aqueous and/or alcoholic and or $CO_2$ extracts.

Evidently, the protopine alkaloid used as well as the benzophenanthridine alkaloid(s) can be used both as isolated alkaloids or respectively as alkaloid mixtures and in form of derivatives or the synthetic analogues thereof.

Moreover, any mixture of plant material, plant juice, extracts of plant material, isolated alkaloids, derivatives thereof and synthetic analogues thereof can be used.

The amount of alkaloids contained in the feed is limited only by the efficiency. The total amount of alkaloids per ton of feed is preferably between 1 mg to 100 g.

The advantages of the inventive feed or feed additive containing protopine alkaloids, preferably α-allocryptopine, particularly in combination with benzophenanthridine alkaloid are documented by the following observations.

The liver of domestic and livestock to which this feed is administered is significantly healthier than that of the respective control groups. This is demonstrated by the dark red color which indicates a lower amount of fat deposition.

The liver of the test animals has a lower weight as % of the body mass, since less fat and other tissues are deposited. This is a positive development, since it indicates less "liver stress."

The test animals have a significantly greater feed intake than those in the control group, so that on the one hand it has to be noted that probably this effect significantly exceeds the level of the effect caused by aromatic substances, and on the other hand it has to be assumed that this advantageous effect is due to improved health of the digestive system of the test animals, especially due to the improved health of the liver.

Due to the better feed intake, the performance of the test animals is improved, also a more advantageous defense against stress and diseases due to the improved liver health is observed.

The content of tryptophan in the portal vein blood is significantly improved compared to that of the control animals which indicates a hepatoprotective effect and thus better health of the liver.

The advantages of the present invention will be explained by means of the examples and the attached drawings where FIG. 1 shows a graphic illustration of the effects achieved with the help of an inventive feed containing alkaloids on the performance and carcass parameters in porkers.

BRIEF DESCRIPTION OF THE DRAWING

The sole FIGURE in this application, FIG. 1 is a series of three sets of bar graphs comparing in pigs fed either a control diet or a feed according to the present invention in terms of (a) thickness of backfat at the last lumbar vertebra, (b) thickness of muscle meat, and (c) the lean meat ratio.

EXAMPLE 1

Pelletized plant parts of *Macleaya cordata* were pulverized and extracted for 12 hours by means of acidified methanol (0.1% HCL) in a Soxhlet extractor.

The extract was analyzed by means of HPLC. HPLC analysis was carried out on a Shimadzu Class VP device provided with an UV-detector SPD-10Avp and a fluorimetric detector RF-10Axl using a Purospher® Star RP-18e reversed phase column. The mobile phase was 1-heptane sulfonic acid/triethyl amine in 25% acetone nitrile in a gradient with 40% acetonitrile. Detection was carried out by means of UV at 285 nm and/or by means of fluorimetry at 327 nm stimulation/577 nm emission. Reference solutions of alkaloids were used in the mobile phase as extern standard. All analyses were carried out three times. As far as the reference alkaloids are concerned, the results of the analyses are listed in Table 1.

EXAMPLE 2

A *Macleaya cordata* extract, prepared by ethanolic aqueous extraction, was dissolved in a concentration of 1 mg/ml in methanol. The solution was subjected to HPLC analysis. Prior to the analysis, it was diluted with the mobile phase. HPLC analysis was carried out as described in example 1. As far as the reference alkaloids are concerned, the results of the analyses are listed in Table 1.

EXAMPLE 3

A further *Macleaya cordata* extract, prepared by ethanolic aqueous extraction, was dissolved in a concentration of 1 mg/ml in methanol. The solution was subjected to HPLC analysis. Prior to analysis, it was diluted with the mobile phase. HPLC analysis was carried out as described in example 1. As far as the reference alkaloids are concerned, the results of the analyses are listed in Table 1.

EXAMPLE 4

In this example, a feed additive consisting of 95% dried *Macleaya cordata* plant parts and of 5% extract from *Macleaya cordata* was analyzed. The sample was extracted for 12 hours with acidified methanol (0.1% HCl) in a Soxhlet extractor. The extract was analyzed by means of HPLC, as described in example 1. As far as the reference alkaloids are concerned, the results of the analyses are also listed in Table 1.

TABLE 1

| | *Macleaya cordata* plant parts (example 1) (mcg/g) | *Macleaya cordata* extract (example 2) (mg/g) | *Macleaya cordata* extract (example 3) (mg/g) | Feed additive (example 4) (mg/g) |
| --- | --- | --- | --- | --- |
| α-allocryptopine | 6.8 ± 0.3 | 21 ± 4 | 6 ± 3 | 15.33 |
| sanguinarin | 6.5 ± 0.3 | 402 ± 19 | 213 ± 9 | 16.5 |
| chelerythrine | 4.7 ± 0.3 | 125 ± 7 | 102 ± 6 | 9.33 |

EXAMPLE 5

Porkers were placed in two stable boxes in same-sex groups of two porkers. The animals were divided in two test groups.

The porkers received conventional feed composed of wheat, barley, HP soy grits, mineral substances, trace elements, vitamins and amino acids, benzophenanthridine alkaloids being added to the feed of test group 1 and α-allocryptopine in combination with benzophenanthridine alkaloids was added to the feed of test group 2. The dosage of the active substances is listed in Table 2. The additive added to the feed of test group 2 contained benzophenanthridine alkaloids and α-allocryptopine in a ratio of about 3:1.

TABLE 2

| test group | alkaloids added | dosage of the active substances |
| --- | --- | --- |
| 1 | benzophenanthridine alkaloid | 0.5 mg/kg |
| 2 | a-allocryptopine + benzophenanthridine alkaloid | 0.8 mg/kg |

At the beginning and at the end of the test period, the animals were weighted once a week and once in two weeks during the test series. Three of the animals were lost during the fattening period. The results of the fattening test from 30 to 105 kg live weight are indicated in Table 3.

TABLE 3

| | test group | |
|---|---|---|
| | 1 | 2 |
| | alkaloids in the feed | |
| | benzophenanthridine alkaloids | α-allocryptopine + benzophenanthridine alkaloids |
| fattening period, days | 86.3 | 81.6 |
| feed intake kg/day | 2.09 | 2.21 |
| weight increase g/day | 874 | 931 |
| feed conversion, kg | 2.39 | 2.38 |
| meat component, % | 59.9 | 59.3 |
| number of meat consistence, points | 53.5 | 54.3 |

As can be seen from Table 3, the animals' level of fattening performance is very high. Test group 2 showed increased feed intake. Test group 1 had a lower weight increase per day, namely 57 g less than test group 2. In a feeding enterprise from 30 kg to 105 kg, these 57 g correspond to about 5 fattening days. Test group 2, which was fed with feed according to the invention, had a higher feed intake and daily weight increase. This is an indication for high appetite, which results from an improved liver health. The meat consistence number of 54.3 in this test group is higher and also indicates a more efficient protein synthesis.

EXAMPLE 6

In two test series the influence of 25, 50 or respectively 100 ppm inventive alkaloid-containing feed was examined in respectively 12×7 male broilers (Ross 308). The feed was conventional, commercial feed for broiler fattening, to which 0, 25, 50 or respectively 100 ppm additive containing alkaloids was added. This additive consisted of a mixture of ground rhizomes of *Sanguinaria canadensis* and plant parts of *Macleaya cordata* and contained about 1.5% Sanguinarin, 0.8% chelerythrine and 0.35% α-allocryptopine. The analyses data of the inventive feed containing alkaloids are listed in Table 4.

TABLE 4

Analyses data of the inventive alkaloid feed as well as of the control feed

| | 0 ppm | 25 ppm | 50 ppm | 100 ppm |
|---|---|---|---|---|
| Additive Content | | | | |
| α-allocryptopine (ppb) | 0 | 230 | 465 | 856 |
| benzophenanthridine alkaloids (ppb) | 0 | 1013 ± 25 | 1963 ± 60 | 3850 ± 85 |
| dry substance (%) | 87.9 ± 0.6 | 88.1 ± 0.7 | 88.0 ± 1.0 | 88.3 ± 0.3 |
| Content/kg (for 890 g dry substance) | | | | |
| ash (g) | 60 ± 1.2 | 60 ± 1.9 | 59 ± 2.0 | 60 ± 1.9 |
| crude protein (g) | 199 ± 3.2 | 200 ± 3.6 | 200 ± 1.0 | 200 ± 5.1 |
| fat (Soxhlet) (g) | 63 ± 1.5 | 64 ± 2.4 | 63 ± 1.5 | 62 ± 1.7 |
| fiber (g) | 28 ± 2.1 | 26 ± 2.0 | 27 ± 0.7 | 27 ± 1.0 |
| total energy (MJ) | 17.4 ± 0.2 | 17.4 ± 0.1 | 17.4 ± 0.2 | 17.4 ± 0.1 |

In Table 5, the growth and carcass parameters are listed.

TABLE 5

| | 0 ppm | | 25 ppm | | 50 ppm | | 100 ppm | |
|---|---|---|---|---|---|---|---|---|
| additive content | Ø | rel[1] | Ø | rel | Ø | rel | Ø | rel |
| body mass (=BM) day 1 (g) | 46 | 100 | 47 | 101 | 46 | 99.1 | 46 | 100 |
| BM day 40 (g) | 2488 | 100 | 2464 | 99.0 | 2526 | 101.5 | 2474 | 99.5 |
| daily weight gain (g) | 62.6 | 100 | 62.0 | 99.0 | 63.6 | 101.6 | 62.3 | 99.5 |
| feed per day (g) | 103 | 100 | 99 | 96.3 | 102 | 99.5 | 102 | 99.6 |
| feed per kg BM (kg) | 1.64 | 100 | 1.60 | 97.6 | 1.61 | 98.2 | 1.64 | 100 |
| slaughter weight (g) | 1799 | 100 | 1774 | 98.6 | 1834 | 101.9 | 1766 | 98.1 |
| carcass yield (%) | 72.1 | 100 | 72.0 | 99.9 | 72.6 | 100.7 | 71.4 | 99.0 |
| color of the liver[2] | 1.19 | 100 | 1.06 | 89 | 1.05 | 88 | 1.07 | 90 |
| water per day (ml) | 202 | 100 | 202 | 100 | 197 | 97.4 | 196 | 97.2 |
| water: feed (ml/g) | 1.97 | 100 | 2.05 | 104 | 1.92 | 97.5 | 1.92 | 97.5 |

[1] Ø = average, rel = relative value (in %)

[2] 1 = dark red (healthy), 2 = yellowish (disease; fatty liver, hepatitis)

The parameters listed in Table 5 show that the slaughter weight was the highest in the test group to which a feed with 50 ppm of additive containing alkaloids was administered, compared to the control group. Feed conversion was improved in those test groups to which feeds with 25 or respectively 50 ppm additive was administered. These results were statistically not significant, since only 4 groups were at disposal and the test was carried out at very high performance level. If more groups had been involved, for example 10 repetitions, the result could have been statistically confirmed.

In all test groups, the animals had a darker liver than the broilers in the control group, which is a clear sign for the hepatoprotective effect of the inventive feed.

Within the framework of these tests, examinations for energy conversion, nitrogen uptake as well as dry substance content of the excrements were carried out. The results are listed in Table 6.

TABLE 6

| additive | 0 ppm | | 25 ppm | | 50 ppm | | 100 ppm | |
|---|---|---|---|---|---|---|---|---|
| content | Ø | rel[(1)] | Ø | rel | Ø | rel | Ø | rel |
| energy conversion | 0.77 | 100 | 0.78 | 101 | 0.78 | 101 | 0.77 | 100 |
| nitrogen uptake | 0.60 | 100 | 0.62 | 103 | 0.61 | 102 | 0.60 | 100 |
| dry substance content of excrements (%) | 28.9 | 100 | 29.2 | 101 | 29.0 | 100 | 29.3 | 101 |

[(1)]Ø = average, rel = relative value (in %)

The test groups, to the feed of which 25 or 50 ppm alkaloids-containing additive was added, in general had the better energy conversion and nitrogen uptake. The measured energy content of the feed, 17.4 MJ/kg together with the energy conversion of 0.77 to 0.78 leads to a content of metabolizable energy in the feed of 13.43 to 13.62 MJ/kg. The excrements of all test groups had a high amount of dry substance, whereas there was practically no difference between the single test groups.

EXAMPLE 7

Influence of α-Allocryptopine and Benzophenanthridine Alkaloids on Selected Parameters of the Protein Conversion Under Standardized Feeding This example illustrates the influence of feed containing α-allocryptopine and benzophenanthridine alkaloids on parameters of the protein metabolism. It is demonstrated that the invention leads to an irreversible in vivo inhibition of AAD (aromatic amino acid decarboxylase) by benzophenanthridine alkaloids so that the supply of the animals with essential nutrients, such as tryptophan and phenylalanine, but also with other essential amino acids is improved, or it is demonstrated that these nutrients can be reduced in commercial feeds by the use of these alkaloids, a fact which had not been known up to now.

Two groups composed of 6 castrated pigs were held in pigsties. At the beginning of the test (day 0), the medium body weight of the animals of the control groups was of 36.08±3.79 kg and that of the animals in the test group of 36.02±3.74 kg. The animals of both groups were fed three times a day with the feed listed in Table 7, the feed of the test group containing α-allocryptopine and benzophenanthridine alkaloids, particularly sanguinarin and chelerythrine, in form of 30 ppm of an additive made of plant material from *Sanguinaria canadensis* and *Macleaya cordata*. The active substance content was 2.2% benzophenanthridine alkaloids and 0.1% α-allocryptopine.

TABLE 7

| Composition of the feed and nutritional value | |
|---|---|
| barley | 64.0% |
| soy grits | 18.9% |
| soy oil | 7.9% |
| wheat bran | 6.4% |
| other ingredients | 2.8% |
| total | 100% |
| crude protein | 16.5% |
| metabolizable energy | 14.0 MJ/kg |
| crude fiber | 5.0% |
| crude ash | 5.5% |
| crude fat | 9.8% |
| lysine | 0.9% |
| methionine/cysteine | 0.5% |
| threonine | 0.6% |
| tryptophan | 0.2% |
| phosphor | 0.6% |
| sodium | 0.1% |
| calcium | 0.9% |

The animals had free access to water, but during the adaptation phase (day 33-39), in which the animals were held individually in a metabolism cage and during N-balance tests carried out subsequently (day 40-49), water was given to satiety only after feeding.

Urine samples were taken once a day, feces samples three times a day. On day 42 and 49, blood was taken from the ear vein in order to determine the ammonium and urea levels.

At the end of the tests, the average body weight of the animals of the test group was slightly increased (76.27±5.11 kg) than that of the animals in the control group (75.09±7.42 kg). Similar observations were made as far as the daily increase in weight is concerned. In the test group, the increase was of 821.3±44.7 and in the control group of 796.1±86.2 g. The daily feed intake achieved by rationed feeding was the same in both groups, thus, the object of the test was realized. Test group: 1775.9±91.5 g; control group 1770.8±120.3 g. The feed conversion of the test group (2.196±0.094) was better than that of the control group (2.237±0.173).

The N-balance study, performed according to scientific principles based on a corrected and thus comparable metabolic body mass (body mass$^{0.75}$ corresponds to the so called metabolic body mass, by which the metabolism of an elephant can be compared with that of a mouse on a scientific base) showed that the N-intake in the control group (2.057±0.011 g/$W^{0.75}$/day) and in the test group (2.062±0.010 g/$W^{0.75}$/day was on the same level, which was an immediate result of the rationed feeding. The determination of N-excretion in the feces gave almost the same values for the control and the test groups, namely 0.360±0.023 g/$W^{0.75}$/day or respectively 0.370±0.044 g/$W^{0.75}$/day.

In N-excretion in urine, however, significant differences were found, namely 0.774±0.094 g/$W^{0.75}$/day in the test group compared to 0.860±0.135 g/$W^{0.75}$/day in the control group. This confirms that N-loss was significantly reduced in the test group by 11%. These data prove, that the feed can be used according to the invention for a significantly improved conversion of the total protein, which was fed, from the feed, which is the object of the invention and has significant economic and environmental advantages.

These data are sustained by N-retention, i.e. the protein accretion in the animal body which was of 0.837±0.133 g/$W^{0.75}$/day in the control group and of 0.918±0.084 g/$W^{0.75}$/ day, which means that the invention leads to an increase in N-retention by 10%. This corresponds to a conversion of the protein from the feed and the protein plants improved by 10%, by means of which the food quality is improved and the nitrogen charge of the ground water is reduced by 10%.

The apparent N-digestibility seems to remain uninfluenced by the feed containing α-allocryptopine and benzophenanthridine alkaloids. The percentages calculated were of 82.53±1.10% in the control group and of 82.07±2.06% in the test group. The data regarding N-conversion show, however, that the values were increased by 10% in the test group (44.52±4.24%) compared to the control group (40.73±6.63), which confirms the in vivo intermediary effect of α-allocryptopine and the benzophenanthridine alkaloids on the protein accretion and the protein conversion of the animals organisms.

As can be seen from the following Table 8, the alkaloid content of the feed has no influence on the development of the ammonium content in the blood samples, which were taken on two days in a distance of one week during the phase of the N-balance tests and a significantly reduced urea level was found in the blood of the test animals. Low urea values are a clear sign for a better conversion of the absorbed protein from the feed and for less efforts of the liver for the detoxication of the toxic nitrogen of feed protein which was not used. This clear effect was not achieved by administration of benzophenanthridine alkaloids only, but resulted form the combination of these with the alkaloid α-allocryptopine. A higher number of animals per group would have lead to statistically significant results.

TABLE 8

Influence of the feed containing alkaloids on the ammonium and urea level in the blood (n = 6)

| | ammonium [μmol/ml] | | urea [mmol/ml] | |
|---|---|---|---|---|
| | day 42 | day 49 | day 42 | day 49 |
| control group | 48.33 ± 5.05 | 39.17 ± 7.98 | 3.87 ± 0.74 | 3.88 ± 0.99 |
| test group | 41.17 ± 3.76 | 39.17 ± 3.97 | 2.92 ± 0.36 | 3.00 ± 0.24 |

It was shown that the addition of α-allocryptopine and benzophenanthridine alkaloids to the feed had clear positive effects in relation to the performance parameters examined, the highest effects being achieved as far as the feed conversion was concerned. Clear differences in relation to the N-balance tests as well as the ammonium and urea level in the blood were found, which due to the low number of test animals could not be statistically confirmed. The reduced values of ammonium and urea in the blood prove that the animals can make better use of the absorbed protein, and thus they are a sign for the better activity of the liver. The observed shift towards a nitrogen reduction, which is an indication for the effects on the protein metabolism, can confirm that the inhibition of AAD by benzophenanthridine alkaloids is an in vivo inhibition and that it is of high economic value.

EXAMPLE 8

Influence of α-Allocryptopine and Benzophenanthridine Alkaloids in Feed on the Feed Intake of Porkers with Unlimited Access to Feed (Ad Libitum Feeding)

Twelve castrated pigs were held in groups of 2 with separate feeding troughs. The feed listed in Table 9 was administered to the control group. The test group received this feed enriched with 30 ppm of the additive mentioned in example 7, consisting of sanguinarin, chelerythrine and α-allocryptopine.

TABLE 9 composition of the feed
(metabolizable energy: 13.5 MJ/kg; 18% crude protein)

| component | % |
|---|---|
| corn | 51 |
| barley | 21 |
| soy grits | 11 |
| fish meal | 8 |
| corn gluten | 6 |
| vitamin/mineral premix | 3 |
| lysine | 0.24 |
| threonine | 0.18 |
| tryptophan | 0.07 |
| methionine | 0.07 |

The following Table 10 shows the results of this test

TABLE 10

Influence of the alkaloid content of the feed on feed intake and growth of porkers (average value ± standard deviation, n = 6)

| | control group | test group |
|---|---|---|
| initial weight, kg | 35.8 ± 1.5 | 35.5 ± 0.8 |
| final weight, kg | 43.8 ± 1.5 | 43.8 ± 1.0 |
| feed intake, g/day | 1779 ± 102 | 1834 ± 68 |
| daily increase in weight, g/day | 1008 ± 80 | 1047 ± 63 |
| feed conversion, g/g | 1.8 ± 0.1 | 1.8 ± 0.1 |

Even though the feed intake of the control group is relatively high, it was further improved in the test group by α-allocryptopine and the benzophenanthridine alkaloids. In the case of ad libitum feeding, a feed intake increased by about 4% was observed in the test group. This is due to an increased tryptophan absorption. The effects of the inhibition of the aromatic amino acid decarboxylase (AAD) by the benzophenanthridine alkaloids and of the hepatoprotective effect of the alkaloid α-allocryptopine are: on the one hand, a higher quantity of tryptophan for an increased serotonin production is at disposal, which has appetite stimulating functions and on the other hand, the appetite and the desire to eat are stimulated by the more efficiently working liver. Thus, the inventive feed leads to an improved and more economic supply of the animal with essential nutrients which otherwise would have to be administered by means of an increased addition to the feed and significantly increased costs and the invention leads furthermore to an health improvement of the animal thanks to the hepatoprotective effect of α-allocryptopine.

In the test group, an increase regarding daily gain of weight compared to the control group was observed. An influence of the content of alkaloids in the feed on feed conversion could not be observed in these tests, since the additional feed was used for an increase in growth.

EXAMPLE 9

The Influence of α-Allocryptopine and Benzophenanthridine Alkaloids in Feed on the Tryptophan and Lysine Levels in the Plasma This example deals with the influence of α-allocryptopine and benzophenanthridine alkaloids on the plasma level of the essential amino acids tryptophan and lysine in porkers. It was the intention to show that benzophenanthridine alkaloids such as sanguinarin and chelerythrine in combination with α-allocryptopine are capable of irreversibly inhibiting undesired bacterial enzymes which decompose essential amino acids, due to which process more essential nutrients such as essential amino acids (tryptophan, lysine, methionine) are at disposal for absorption. The test was supposed show whether the reduced, undesired decomposition of essential amino acids, accordingly to the invention results in increased in vivo values in the blood, which are later at disposal for growth and performance or which no longer have to be added to the feed, or respectively only have to be added in reduced quantities.

Twelve castrated pigs were held in separate metabolism cages. Both the control group and the test groups were comprised of 6 animals. The composition of the feed was the same for the control and the test groups as already described in example 8. In order to allow for a direct comparison of the result, the feeding was restrictive, namely set on 95 g/kg metabolic body weight ($BW^{0.75}$).

The adaptation phase of the animals lasted 10 days, the subsequent test phase 7 days. On the last day, blood samples were taken before feeding and one hour after feeding in order to perform the tryptophan and lysine analysis.

As can be seen from Table 11, the tests regarding the increase in weight and the feed conversion showed better results for the test group than for the control group.

TABLE 11 impact of α-allocryptopine and benzophenanthridine alkaloids in feed on the growth of porkers (average value ± standard deviation, n = 6)

|  | control group | test group |
|---|---|---|
| initial weight, kg | 37.0 ± 0.6 | 36.5 ± 0.2 |
| final weight, kg | 45.3 ± 0.9 | 44.9 ± 1.2 |
| daily increase in weight, g/day | 828 ± 25 | 841 ± 28 |
| feed conversion, g/g | 1.86 ± 0.06 | 1.84 ± 0.06 |

The examination of the preprandial and postprandial tryptophan and lysine concentrations in the plasma showed an significant increase for both groups. The postprandial tryptophan and lysine concentrations in the plasma were significantly increased in the test group compared to the control group. This shows that the inhibition of the amino acid decarboxylases by benzophenanthridine alkaloids, particularly sanguinarin and α-allocryptopine is an in vivo inhibition, that the "protected" tryptophan and lysine in the small intestine are actively at disposition for absorption and that feed containing α-allocryptopine and benzophenanthridine alkaloids allow for a better use of tryptophan and lysine in the feed.

EXAMPLE 10

Influence of α-Allocryptopine and Benzophenanthridine Alkaloids on Lactating Sows and the Litter Performance, caused by Increased Feed Consumption and Increased in vivo Disposal of Nutrients Due to the Effects of the Inventive Feed Shown in Examples 7 to 9

This example shows the influence of α-allocryptopine and benzophenanthridine alkaloids in the feed on the feed intake of lactating sows and on the performance of the sow and its litters during lactation period.

106 sows (72 crossed Landrace×Large White, 34 Leicoma) between the first and the ninth parity (3.6+0.2 average value ±standard deviation) were accommodated corresponding to their parities. All animals received the same corn and soy feed (metabolizable energy 13.8 MJ/kg; 17.5% XP) wherein in the case of the two test groups 30 ppm or respectively 50 ppm of the additive mentioned in example 8 were added to the feed. The administration of this feed started 4 days before farrowing and was stopped on day 20 thereafter (discontinuation).

As far as the feed intake is concerned, a slight increase compared to the control group was observed in the test groups. The survival rate of the piglets, measured on day 20, was not influenced by the content of alkaloids. When the litters of the old sows with three and more births were compared, no differences regarding an increase in weight of the litter could be observed. When first litter sows and second litter sows of the test group with benzophenanthridine alkaloids and α-allocryptopine are compared, the results are totally different. Significant increases as far as the increase in weight of the litters of the test groups compared to the control groups is concerned, are observed. Thus, one can draw the conclusion that the addition of α-allocryptopine and benzophenanthridine alkaloids to the feed has positive influences on the increase in weight of the piglets of a first litter sow during lactation.

Due to the AAD inhibition, a larger amount of tryptophan is at disposal which leads to an increased feed intake by the sows. In combination with more lysine as essential nutrient for protein synthesis, this leads to an increased milk production, which again has positive influences on the growth of the piglets.

EXAMPLE 11

Influence of α-Allocryptopine and Benzophenanthridine Alkaloids in the Feed on the Performance and Carcass Parameters of Porkers The feed (metholizable energy 13.8 MJ/kg; 1.00% lysine) was composed of the following components:

| | |
|---|---|
| barley | 46% |
| wheat | 35.40% |
| soy extraction grits | 11.40% |
| fish meal | 2.21% |
| soy oil | 2.00% |
| feed lime | 1.00% |

-continued

| | |
|---|---|
| dicalcium phosphate | 0.74% |
| salt | 0.25% |
| premix: trace elements + vitamins | 1.00% |

30 ppm of an additive, consisting of plant material of *Sanguinaria canadensis* and *Macleaya cordata* were added to the feed of the test group. The reference alkaloids contained therein are mainly sanguinarin and chelerythrine as well as α-allocryptopine. All animals were fed twice a day semi ad libitum and had free access to water at all times.

The medium body weight at the start and at the end of the tests was as follows.

| | control group | | test group | |
|---|---|---|---|---|
| | start | end | start | end |
| test | 30.1 ± 0.5 | 100.9 ± 7.4 | 30.3 ± 0.9 | 100.4 ± 5.4 |

In this test, no differences regarding the daily increase of weight, the feed intake and the feed conversion no differences is between the control group and the test group could be observed. Some carcass parameters of the test group, however, were significantly better than those of the control group, particularly a significantly more muscle flesh as well as a significantly reduced amount of back fat could be observed.

The results of the test are illustrate in FIG. 1. Dark bars represent the results of the control group, dark hatched bars those of the test group. FIG. 1 shows the significant positive results regarding the carcass quality, such as significantly reduced thickness of the back fat and improved muscle area at the ribs, which can be achieved by the feed containing alkaloids according to this invention.

It was shown that a connection between the lean flesh and the tryptophan and lysine at disposal can be found, i.e. that the use of the feed containing alkaloids leads to an improved protein balance due to the optimized balance of the essential amino acids and in consequence to more lean flesh and more milk protein.

The invention claimed is:

1. An animal feed comprising conventional feedstuffs selected from the group consisting of cereals or cereal products, maize, proteins and essential amino acids, vitamins, mineral additives, salts, phosphates, lime and enzymes; or a feed additive for the preparation of such feed, wherein the feed or the feed additive comprises:
    (a) at least one benzophenanthridine alkaloid, being of natural or synthetic origin; and
    (b) α-allocryptopine in an effective amount to serve as a performance enhancer and appetite stimulant for livestock, the α-allocryptopine being of natural or synthetic origin, wherein the weight ratio of the at least one benzophenanthridine alkaloid and the α-allocryptopine is selected from the group consisting of 3:1, 1013:230, 1963:465, and 3850:856.

2. An animal feed comprising conventional feedstuffs selected from the group consisting of cereals or cereal products, maize, proteins and essential amino acids, vitamins, mineral additives, salts, phosphates, lime and enzymes; or a feed additive for the preparation of such feed, wherein the feed or the feed additive comprises:
    (a) at least one benzophenanthridine alkaloid, being of natural or synthetic origin; and
    (b) α-allocryptopine in an effective amount to serve as a performance enhancer and appetite stimulant for livestock, the α-allocryptopine being of natural or synthetic origin, wherein the weight ratio of the at least one benzophenanthridine alkaloid and the α-allocryptopine is about 3:1.

3. An animal feed comprising conventional feedstuffs selected from the group consisting of cereals or cereal products, maize, proteins and essential amino acids, vitamins, mineral additives, salts, phosphates, lime and enzymes; or a feed additive for the preparation of such feed, wherein the feed or the feed additive comprises:
    (a) a benzophenanthridine alkaloid mixture of natural or synthetic origin comprising sanguinarine and chelerythrine wherein the animal feed additive comprises as the benzophenanthridine alkaloid mixture, 1.5% sanguinarine and 0.8% chelerythrine; and
    (b) α-allocryptopine being of natural or synthetic origin wherein the feed additive comprises the α-allocryptopine in an amount of 0.35% aa an effective amount to serve as a performance enhancer and appetite stimulant for livestock.

4. The feed or feed additive according to claim 3 wherein the α-allocryptopine, the sanguinarine, and the chelerythrine are contained in the feed in an amount of 25 to 50 ppm.

5. The feed or feed additive according to claim 4 wherein the α-allocryptopine, the sanguinarine, and the chelerythrine are contained in the feed in an amount of 50 ppm.

6. A method of enhancing the performance and stimulating the appetite of livestock, which comprises the step of administering to the livestock, an animal feed comprising conventional feedstuffs selected from the group consisting of cereals or cereal products, maize, proteins and essential amino acids, vitamins, mineral additives, salts, phosphates, lime and enzymes; or a feed additive for the preparation of such feed, wherein the feed or the feed additive comprises:
    (a) at least one benzophenanthridine alkaloid, being of to natural or synthetic origin; and
    (b) α-allocryptopine in an effective amount to serve as a performance enhancer and appetite stimulant for livestock, the α-allocryptopine being of natural or synthetic origin, wherein the weight ratio of the at least one benzophenanthridine alkaloid and the α-allocryptopine is selected from the group consisting of 3:1, 1013:230, 1963:465, and 3850:856.

7. A method of enhancing the performance and stimulating the appetite of livestock, which comprises the step of administering to the livestock, an animal feed comprising conventional feedstuffs selected from the group consisting of cereals or cereal products, maize, proteins and essential amino acids, vitamins, mineral additives, salts, phosphates, lime and enzymes; or a feed additive for the preparation of such feed, wherein the feed or the feed additive comprises:
    (a) at least one benzophenanthridine alkaloid, being of to natural or synthetic origin; and
    (b) α-allocryptopine in an effective amount to serve as a performance enhancer and appetite stimulant for livestock, the α-allocryptopine being of natural or synthetic origin, wherein the weight ratio of the at least one benzophenanthridine alkaloid and the α-allocryptopine is about 3:1.

8. A method of enhancing the performance and stimulating the appetite of livestock, which comprises the step of administering to the livestock, an animal feed comprising conventional feedstuffs selected from the group consisting of cereals or cereal products, maize, proteins and essential amino acids, vitamins, mineral additives, salts, phosphates, lime and enzymes; or a feed additive for the preparation of such feed, wherein the feed or the feed additive comprises:
(a) a benzophenanthridine alkaloid mixture of natural or synthetic origin comprising sanguinarine and chelerythrine wherein the feed additive comprises as the benzophenanthridine alkaloid mixture, 1.5% sanguinarine and 0.8% chelerythrine; and
(b) α-allocryptopine being of natural or synthetic origin, wherein the feed additive comprises the α-allocryptopine in an amount of 0.35% as an effective amount to serve as a performance enhancer and appetite stimulant for livestock.

9. The method of enhancing the performance and stimulating the appetite of livestock defined in claim 8 wherein the feed additive contained in the feed comprises α-allocryptopine, sanguinarine and chelerythrine and the feed comprises the additive in an amount of 25 to 50 ppm.

10. The method of enhancing the performance and stimulating the appetite of livestock defined in claim 9 wherein the feed additive contained in the feed comprises α-allocryptopine, sanguinarine and chelerythrine and the feed comprises the additive in an amount of 50 ppm.

* * * * *